United States Patent
Wysong et al.

(10) Patent No.: US 6,225,260 B1
(45) Date of Patent: May 1, 2001

(54) QUATERNARY AMMONIUM SALTS OF A SULFONYLUREA

(75) Inventors: Robert D. Wysong, Wilmington, DE (US); Chia-Chung Chen, Nantou Hsien (TW); Chuen-Ing Tseng, Lawrenceville; Arturo A. Tirol, Kendall Park, both of NJ (US)

(73) Assignees: Lonza Inc., Fair Lawn, NJ (US); E. I. DuPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/315,391

(22) Filed: May 20, 1999

Related U.S. Application Data

(63) Continuation-in-part of application No. PCT/US97/21383, filed on Nov. 19, 1997.
(60) Provisional application No. 60/117,222, filed on Jan. 25, 1999, and provisional application No. 60/032,019, filed on Nov. 22, 1996.

(51) Int. Cl.$^7$ .......................... A01N 25/30; A01N 47/36; C07D 239/69; C07D 251/30
(52) U.S. Cl. .......................... 504/212; 504/213; 544/189; 544/194; 544/321; 544/331
(58) Field of Search ................... 544/321, 331, 544/189, 194, 199; 504/212, 213

(56) References Cited

U.S. PATENT DOCUMENTS

| | | | |
|---|---|---|---|
| 4,479,821 | * | 10/1984 | Meyer et al. .......................... 544/211 |
| 4,681,619 | * | 7/1987 | Meyer et al. .......................... 544/211 |

FOREIGN PATENT DOCUMENTS

| | | | |
|---|---|---|---|
| 2073135 | | 1/1993 | (CA) . |
| 0 521 500 | * | 7/1993 | (EP) . |
| 00/44226 | | 8/2000 | (WO) .............................. A01N/47/36 |

\* cited by examiner

*Primary Examiner*—Mukund J. Shah
*Assistant Examiner*—Venkataraman Balasubramanian
(74) *Attorney, Agent, or Firm*—Darby & Darby

(57) ABSTRACT

The present invention provides a compound comprising a quaternary ammonium salt of a sulfonylurea having the formula

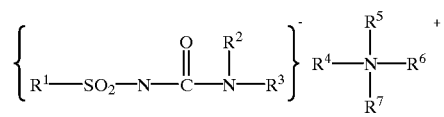

wherein $R^1$ is a substituted or unsubstituted phenyl, heterocyclic ring, or phenoxy, or —$N(CH_3)(SO_2CH_3)$; $R^2$ is H or $CH_3$; $R^3$ is a substituted or unsubstituted pyrimidine or a substituted or unsubstituted triazine; $R^4$ and $R^5$ are independently unsubstituted or hydroxy substituted linear or branched $C_1$–$C_4$ alkyls, —$(CH_2CH_2O)_mCH_2CH_2OH$, or —$(CH_2CHCH_3O)_mCH_2CHCH_3OH$ where m is 1 to 10; $R^6$ is a substituted or unsubstituted benzyl, ethylbenzyl, naphthylmethyl, or linear or branched $C_1$–$C_{22}$ alkyl; $R^7$ is a substituted or unsubstituted, linear or branched $C_8$–$C_{22}$ alkyl or —$R^{13}(O)_n(C_6H_5)R^{14}$ where n is 0 or 1; $R^{13}$ is a substituted or unsubstituted $C_1$–$C_8$ alkyl or $C_1$–$C_8$ alkoxyalkyl; and $R^{14}$ is a substituted or unsubstituted, linear or branched $C_1$–$C_{12}$ alkyl. Also, a method of preparing a quaternary ammonium salt of a sulfonylurea is provided. The method comprises contacting a quaternary ammonium hydroxide and a sulfonylurea to form the quaternary ammonium salt of the sulfonylurea. The quaternary ammonium salts of a sulfonylurea are useful as herbicides, fungicides, and plant growth regulating agents.

19 Claims, 2 Drawing Sheets

QUATERNARY AMMONIUM SALTS OF A SULFONYLUREA

This application is a continuation-in-part of U.S. Ser. No. 60/117,222, filed Jan. 25, 1999, and PCT Application Serial No. PCT/US97/21383, filed Nov. 19, 1997, which claims priority from U.S. Ser. No. 60/032,019, filed Nov. 22, 1996.

FIELD OF THE INVENTION

This invention relates to quaternary ammonium salts of a sulfonylurea, methods for preparing quaternary ammonium salts of a sulfonylurea, and the use of such compounds as pesticides, herbicides, fungicides, and plant growth regulating agents.

BACKGROUND OF THE INVENTION

Sulfonylureas are known to be highly effective as herbicides and plant growth regulators. See, for example, U.S. Pat. Nos. 4,127,405; 4,169,719; 5,391,539; 5,488,029; 5,508,441; 5,580,842; 5,591,694; 5,599,769; 5,612,286; 5,635,450; 5,658,854; 5,688,745; 5,696,053; 5,714,436; and 5,747,421. However, aqueous solutions of sulfonylureas frequently degenerate within days and, therefore, cannot be stored for long periods of time.

There have been previous attempts to stabilize sulfonylureas in aqueous suspension compositions. For example, Sandell, U.S. Pat. No. 4,599,412, discloses a process for the preparation of solution formulations of sulfonylureas containing an agriculturally suitable cation, such as ammonium or substituted ammonium. Sandell also generally discloses that ammonium and quaternary ammonium salts of sulfonylureas can be prepared by treating the corresponding N-protonated sulfonylurea with an ammonium salt solution. Sandell notes, however, that these compounds are still susceptible to the degradative effects of moisture and impurities present in at least trace quantities in all practical solvent systems.

Hyson, U.S. Pat. No. 4,936,900, discloses compositions consisting essentially of a sulfonylurea and a carboxylic or an inorganic acid. No quaternary ammonium salts are disclosed.

Ort et al., U.S. Pat. No. 5,688,745, discloses salts of a sulfonylurea formed from bases, such as alkali metal carbonates, alkali metal hydroxides, alkaline earth metal hydroxides, ammonia, and ethanolamine, or acids, such as hydrochloric acid, nitric acid, trichloroacetic acid, acetic acid, and palmitic acid.

Schnabel et al., U.S. Pat. No. 5,696,053, is directed to a salt of a sulfonylurea containing a metal or ammonium ion.

Föry et al., PCT Publication No. WO 97/41112, discloses a salt of a sulfonylurea containing an alkali metal or alkaline earth metal atom.

SUMMARY OF THE INVENTION

Applicants have discovered quaternary ammonium salts of a sulfonylurea having high water solubility and high hydrolytic stability, and a method of preparing such compounds comprising contacting a quaternary ammonium hydroxide with a sulfonylurea to form the quaternary ammonium salt of a sulfonylurea.

Pesticidal, herbicidal, fungicidal, and plant growth regulating compositions comprising an effective amount of one or more of the quaternary ammonium salts of a sulfonylurea are a further embodiment of the present invention.

Still another embodiment is a method of controlling plants or fungi comprising applying an effective amount of one or more of the quaternary ammonium salts of a sulfonylurea of the present invention to the plants or fungi, the seeds of the plants, or the area on which the plants or fungi grow. Yet another embodiment is a method of regulating the growth of plants comprising applying an effective amount of one or more of the quaternary ammonium salts of a sulfonylurea of the present invention to the plants.

DETAILED DESCRIPTION OF THE INVENTION

Figure 1:
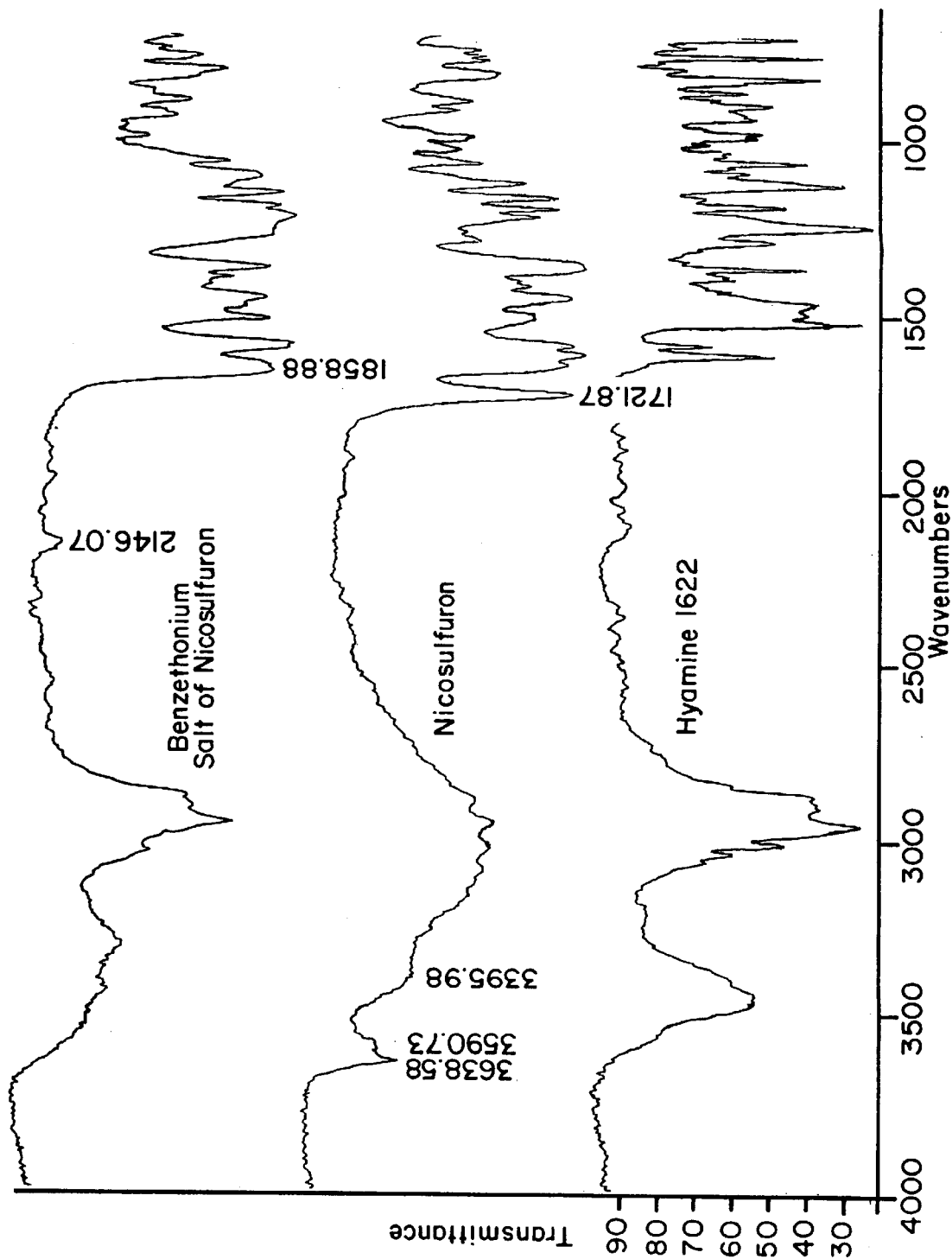
FIG. 1 are FT-IR spectra over the range 500 to 4,000 wavenumbers of benzethonium salt of nicosulfuron, nicosulfuron, and benzethonium chloride.

The present invention encompasses quaternary ammonium salts of a sulfonylurea having the formula

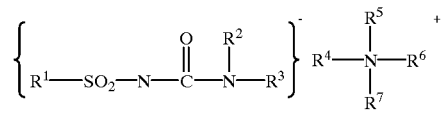

wherein $R^1$ is a substituted or unsubstituted phenyl, heterocyclic ring, or phenoxy, or —N(CH$_3$)(SO$_2$CH$_3$); $R^2$ is H or CH$_3$; $R^3$ is a substituted or unsubstituted pyrimidine or a substituted or unsubstituted triazine; $R^4$ and $R^5$ are independently unsubstituted or hydroxy substituted linear or branched $C_1$–$C_4$ alkyls, —(CH$_2$CH$_2$O)$_m$CH$_2$CH$_2$OH, or —(CH$_2$CHCH$_3$O)$_m$CH$_2$CHCH$_3$OH where m is 1 to 10; $R^6$ is a substituted or unsubstituted benzyl, ethylbenzyl, methylnaphthyl, or linear or branched $C_1$–$C_{22}$ alkyl; $R^7$ is a substituted or unsubstituted, linear or branched $C_1$–$C_{22}$ alkyl or —R$^{13}$(O)$_n$(C$_6$H$_5$)R$^{14}$ where n is 0 or 1; $R^{13}$ is a substituted or unsubstituted $C_1$–$C_8$ alkyl or $C_1$–$C_8$ alkoxyalkyl; and $R^{14}$ is a substituted or unsubstituted, linear or branched $C_1$–$C_{12}$ alkyl.

Preferably, $R^1$ is

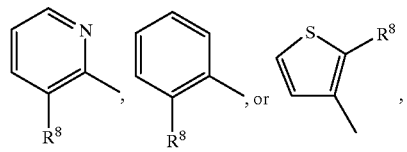

wherein $R^8$ is CON(CH$_3$)$_2$, SO$_2$R$^{11}$, or CO$_2$R$^{12}$; and $R^{11}$ and $R^{12}$ are independently $C_1$–$C_3$ alkyls. More preferably, $R^1$ is 3-(dimethylamino)carbonyl-2-pyridinyl, 3-(ethylsulfonyl)-2-pyridinyl, 2-carbomethoxyphenyl, or 2-carbomethoxythienyl.

Preferably, $R^3$ is

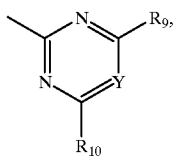

wherein $R^9$ is $CH_3$, $OCH_3$, $OCH_2CH_3$, or $NHCH_3$; Y is CH or N; and $R^{10}$ is $CH_3$ or $OCH_3$. More preferably, $R^3$ is 4,6-dimethoxy-2-pyrimidinyl or 4-methoxy-6-methyl-1,3,5-triazin-2-yl.

Most desirably, the sulfonylurea is 2-[[[[(4,6-dimethoxy-2-pyrimidinyl)amino]carbonyl]amino]suflonyl]-N,N-dimethyl-3-pyridinecarboxamide (nicosulfuron); N-[[(4,6-dimethoxy-2-pyrimidinyl)amino]carbonyl]-3-(ethylsulfonyl)-2-pyridinesulfonamide (rimsulfuron); methyl 2-[[[[(4-methoxy-6-methyl)-1,3,5-triazin-2-yl)amino]carbonyl]amino]sulfonyl]benzoate (metsulfuron-methyl); methyl 2-[[[[(4-methoxy-6-methyl-1,3,5-triazin-2-yl)methylamino]carbonyl]amino]sulfonyl]benzoate (tribenuron-methyl); 3-[[[[(4-methoxy-6-methyl-1,3,5-triazin-2-yl)amino]carbonyl]amino]sulfonyl]-2-thiophenecarboxylic (trifensulfuron-methyl); 2-chloro-N-[[(4-methoxy-6-methyl-1,3,5-triazin-2-yl)amino]carbonyl]benzenesulfonamide (chlorsulfuron); methyl 2-[[[[(4-ethoxy-6-(methylamino)-1,3,5-triazin-2-yl)amino]carbonyl]amino]sulfonyl]benzoate (ethametsulfuron-methyl); methyl 2 -[[[[[4-(dimethylamino)-6-(2,2,2-trifluoroethoxy)-1,3,5-triazin-2-yl]amino]carbonyl]amino]sulfonyl]-3-methylbenzoate (triflusulfuron-methyl); ethyl 2-[[[[(4-chloro-6-methoxy-2-pyrimidinyl)amino]carbonyl]amino]sulfonyl]benzoate (chlorimuron ethyl); methyl 2-[[[[(4,6-dimethyl-2-pyrimidinyl)amino]carbonyl]amino]sulfonyl]benzoate (sulfometuron-methyl); N-[[(4,6-dimethoxypyrimidine-2-yl)amino]carbonyl]-1-methyl-4-(2-methyl-2H-tetrazol-5-yl)-1H-pyrazole-5-sulfonamide (azimsulfuron); bensulfuron-methyl; or flupyrsulfuron-methyl. The foregoing compounds are available from DuPont Agricultural Products of Wilmington, Del. Other desirable sulfonylureas include, but are not limited to, amidosulfuron, iodosulfuron, and ethoxysulfuron available from Hoechst Schering Agrevo GmbH of Berlin, Germany; prosulfuron, oxasulfuron, primisulfuron, triasulfuron, and cinosulfuron available from Novartis Crop Protection AG of Basel, Switzerland; flazasulfuron available from Ishihara Sangyo of Kusatsu, Japan; halosulfuron available from Monsanto of St. Louis, Mo.; and imazosulfuron available from Takeda Chemical Industries of Osaka, Japan.

$R^{13}$ of the quaternary ammonium group is preferably —$CH_2CH_2OCH_2CH_2$— and $R^7$ is preferably [2-[2-(4-diisobutylphenoxy)ethoxy]ethyl]. More preferably, the quaternary ammonium group is [2-[2-(4-diisobutylphenoxy)ethoxy]ethyl]dimethylbenzyl ammonium (also known as benzethonium and available as benzethonium chloride or Hyamine 1622™); a dialkyl ($C_8$ to $C_{22}$) dimethylammonium; a dialkyl ($C_8$ to $C_{22}$) methyl poly(oxyethyl) ammonium; an alkyl ($C_8$ to $C_{22}$) benzyldimethyl ammonium; an alkyl ($C_8$ to $C_{22}$) trimethylammonium; a dialkyl ($C_8$ to $C_{22}$) dihydroxyethyl ammonium; a dialkyl ($C_8$ to $C_{22}$) methyl hydroxyethyl ammonium; or an alkyl ($C_8$ to $C_{22}$) methyl dihydroxyethyl ammonium.

Most preferably, the quaternary ammonium group is [2-[2-(4-diisobutylphenoxy)ethoxy]ethyl]dimethylbenzyl ammonium; N,N-didecyldimethylammonium (available as Bardac™ 22); N,N-decylisononyldimethylammonium (available as Bardac 21™); N,N-decyloctyldimethylammonium (available as Bardac™ 20); N,N-dioctyldimethylammonium (available as Bardac™ LF); hexadecyltrimethylammonium (available as Barquat™ CT-29); octadecyldimethylbenzylammonium (available as Carsoquat™ SDQ-25); N,N-didecyl-N-methyl-poly(oxyethyl)ammonium (available as Bardap™ 26); or alkyl ($C_{10}$–$C_{18}$) dimethylbenzylammonium (available as Barquat™ 80-28). The foregoing compounds are available from Lonza Inc. of Fair Lawn, N.J.

Alternatively, the quaternary ammonium salts of a sulfonylurea may have the formula

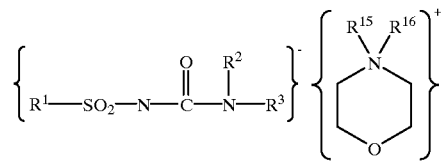

wherein $R^1$, $R^2$, and $R^3$ are defined as above; $R^{15}$ is a substituted or unsubstituted, linear or branched $C_8$–$C_{22}$ alkyl; and $R^{16}$ is a substituted or unsubstituted, linear or branched $C_1$–$C_{22}$ alkyl. Preferably, $R^{16}$ is a substituted or unsubstituted, linear or branched $C_1$–$C_3$ alkyl.

The quaternary ammonium salts of a sulfonylurea of the present invention are highly water soluble. For example, a 50% aqueous solution of benzethonium salts of nicosulfuron may be prepared.

Another embodiment of the invention is an herbicidal, fungicidal, and/or plant growth regulating agent concentrate comprising from about 0.1% to about 99%, preferably, 0.2% to 95%, by weight of one or more of the quaternary ammonium salts of a sulfonylurea of the present invention based upon 100% of total concentrate. Generally, the herbicidal concentrate further comprises from about 1% to about 99.9%, preferably from about 5% to about 99.8%, by weight of a solid or liquid formulation adjuvant and up to 25%, preferably from about 0.1% to 25%, by weight of one or more surfactants.

A surface active agent may be added to the composition of the present invention to increase herbicidal efficacy. The surface active agent may be an anionic surfactant, nonionic surfactant, or any combination of any of the foregoing. Anionic surfactants include, but are not limited to, alkylnaphthalene sulfonates, alkylbenzene sulfonates, alpha olefin sulfonates, calcium lignosulfonates, aluminum lignosulfonates, dodecylbenzene sulfonates, naphthalene/formaldehyde condensates, sulfosuccinates, alkyl sulfates, aryl sulfates, alkyl phosphates, aryl phosphates, ethoxylated lignosulfonates, ethoxylated alkyl sulfonates, ethoxylated distyrylphenol sulfates, ethoxylated tristyrylphenol sulfates, ethoxylated distyrylphenol phosphates, ethoxylated tristyrylphenol phosphates, and any combination of any of the foregoing. Nonionic surfactants include, but are not limited to, polyoxyethylene alcohols, tristyrylphenols, nonyl phenols, octyl phenols, nonyl esters, octyl esters, nonyl diesters, octyl diesters, nonyl sorbitol esters, octyl sorbitol esters, polyoxyethylene/propylene block copolymers, ethoxylated siloxanes, acetylenic diols, polyglucosides, and any combination of any of the foregoing. A preferred nonionic surfactant is poly(oxyethylene)sorbitan ether monolaurate, available as Tween 20® from ICI Surfactants of Wilmington, Del. Other preferred surfactants include, but are not limited to, nonylphenolpolyethoxyethanols, castor oil, polyglycol ethers, polypropylene/polyethylene oxide adducts, polyethylene glycol and octylphenoxypolyethoxyethanol. Other surfactants as described in *McCutcheon's Detergents and Emulsifiers Annual,* McCutcheon Publishing Corp., Ridgewood, N.J. (1997), may also be added.

The composition may include additional herbicides, such as bromoxanil and acetochlor. Herbicides that may be used in the compositions with the quaternary ammonium salts of a sulfonylurea include partner herbicides, such as a hormonal, anticholine esterase, or glyphosate. Examples of hormonal herbicides include, but are not limited to, phenoxies, such as (2,4-dichlorophenoxy)acetic acid (2,4D) derivatives and 4-chloro-2-methylphenoxy acetic acid (MCPA). Examples of anticholine esterase herbicides include, but are not limited to, organophosphorous herbicides, such as anilofos.

The compositions may also comprise further auxiliaries, such as wetting agents, adhesives, emulsifiers, preservatives, fillers, carriers, viscosity and pH regulators, binders, tackifiers, fertilizers, and other active ingredients. For example, herbicidal active substances, such as those described in *The Pesticide Manual,* 11$^{th}$ edition, edited by C. Tomlin and published by The British Crop Protection Council, Surrey, UK (1997) and in *Federally Registered Pesticides,* published by North American Compendiums, Inc., Port Huron, Mich. (1998), may be included in the composition.

Other conventional adjuvants may be added to the composition for different applications as known to those of ordinary skill in the art.

The quaternary ammonium salt of a sulfonylurea may be incorporated into different formulations including, but not limited to, granules, pellets, tablets, wettable powders, wettable dusts, microencapsulated materials, impregnated materials, emulsifiable concentrates, flowable concentrates, soluble concentrates, and ready-to-use solutions. The concentrates, granules, pellets, tablets, dusts, and other materials may be diluted with a solvent, such as water, to form a use dilution of the quaternary ammonium salt of a sulfonylurea which may be used as a pesticide, fungicide, herbicide, and/or plant growth regulating agent. The solvent may be an organic solvent. Example of organic solvents include, but are not limited to, natural crop oils such as soybean oil, corn oil, cottonseed oil, sunflower oil and epoxidized or methylated derivatives thereof; propylene carbonate; triethyl phosphate; n-alkyl pyrrolidones; and crop oil esters, such as methylsoyate available from Henkel Corp. of Ambler, Pa., and acetates such as heptyl acetate and Exxates® available from Exxon Chemicals Co. of Houston, Tex.; and mixtures thereof. Hydrophobic oils such as diisodecyl adipate and $C_8-C_{12}$ alcohols may be used for spreading in rice paddy applications.

Aqueous solutions of the present invention may optionally contain antifreezing agents, such as glycols, including, but not limited to, propylene glycol.

Also, the invention includes a method of controlling plants or fungi comprising applying a solution of an effective amount of one or more of the quaternary ammonium salts of a sulfonylurea to the plants or fungi, the seeds of the plants, or the area on which the plants or fungi grow. The solution may also be applied to plants to regulate their growth.

Generally the quaternary ammonium salt of a sulfonyl urea is applied at a rate ranging from about 0.1 to about 1,000 g/ha (grams/hectare) to plants or fungi, the seeds of the plants, and/or the area on which the plants or fungi grow.

Quaternary ammonium salts of a sulfonylurea, including the quaternary ammonium salts of a sulfonylurea described above, may be prepared from a sulfonylurea and a quaternary ammonium hydroxide by mixing the sulfonylurea and the quaternary ammonium hydroxide. Broadly the molar ratio of the quaternary ammonium hydroxide to the sulfonylurea used in the reaction ranges from about 0.3 to about 3.0. Preferably, the molar ratio ranges from about 0.5 to about 1.5 and more preferably from about 0.8 to about 1.2. The mixing is for a period sufficient to effectively mix the quaternary ammonium hydroxide and the sulfonylurea. It will depend on the size of the mixing vessel and the amounts of the sulfonylurea and the quaternary ammonium hydroxide. Preferably, the mixing is effected at a temperature of from about −25 to about 125° C., more preferably, at a temperature of from about 0 to about 50° C.

The quaternary ammonium hydroxide may be prepared by methods known in the art, such as that disclosed in U.S. Pat. No. 5,399,762. One method is by mixing a quaternary ammonium halide, preferably the chloride, with an alkali metal hydroxide, preferably potassium hydroxide. The alkali metal hydroxide may be dissolved in a solvent such as water; an alcohol, such as methanol, ethanol, isopropanol, propylene glycol, ethylene glycol, and other polyols; and/or other polar organic solvents, such as acetonitrile, dimethylformamide, and alkyl ethers. Preferred solvents include, but are not limited to, methanol, ethanol, and isopropanol. For preparing solid sulfonylurea quaternary ammonium compounds, low molecular weight organic solvents are preferable. The mixing is for a time sufficient to effectively mix the quaternary ammonium salt and the alkali metal hydroxide. It will depend on the size of the mixing vessel and the amounts of the quaternary ammonium salt and the alkali metal hydroxide. The mixture may be filtered to remove any alkali metal halide which form during the preparation of the quaternary ammonium hydroxide.

DESCRIPTION OF THE PREFERRED EMBODIMENTS

The following examples illustrate the invention without limitation. All parts and percentages are given by weight unless otherwise indicated.

EXAMPLE 1

Benzethonium salt of nicosulfuron was prepared as follows.

15.0 g. of potassium hydroxide (85%, 0.227 mol) were added to 75 g. of ethanol in a 500 ml reaction flask. The mixture was stirred until a clear and colorless solution was obtained. 100.0 g. of Hyamine 1622™ (benzethonium chloride, 0.223 mol) were added to the solution. The solution was stirred for 2 hours at room temperature. The resulting slurry was filtered through a filter funnel to remove potassium chloride salt. The salt cake formed on the filter funnel was rinsed with 25 ml of cold ethanol. The filtrates were combined. The concentration of the benzethonium hydroxide in the solution was determined to be 50.3% by titration with sodium lauryl sulfate.

39.6 g. (0.047 mol) of the quaternary ammonium hydroxide solution were placed in a 100 ml reaction flask. 20.4 g. of nicosulfuron (0.047 mol) were added to the reaction flask. The contents of the flask were stirred at room temperature for 15–30 minutes until a clear solution was obtained. After stirring, the reaction flask was cooled with an ice bath. The quaternary ammonium salts of the sulfonylurea in the solution solidified during cooling. The solvent was removed and the solid was dried under vacuum at room temperature to yield 39.58 g. of product. The product was a light yellow powder.

Elemental analysis on the benzethonium salt of nicosulfuron was performed. The benzethonium salt of nicosulfuron prepared contained 60.21% carbon, 7.23% hydrogen, 11.65% nitrogen, and 3.87% sulfur. Based on the molecular formula, the benzethonium salt of nicosulfuron contains 61.39% carbon, 7.19% hydrogen, 11.94% nitrogen, and 3.98% sulfur.

The melting point of the product was determined to be from about 60 to about 64° C., compared to from about 141 to about 144° C. for nicosulfuron. At room temperature, the water solubility of the quaternary ammonium salt of the sulfonylurea is over 50%, while the water solubility for nicosulfuron alone is only 1.2% at a pH of 7.

FT-IR spectra of the benzethonium salt of nicosulfuron, nicosulfuron, and benzethonium chloride over the range 500 to 4,000 wavenumbers were obtained. The results are shown in FIG. 1.

Figure 2:
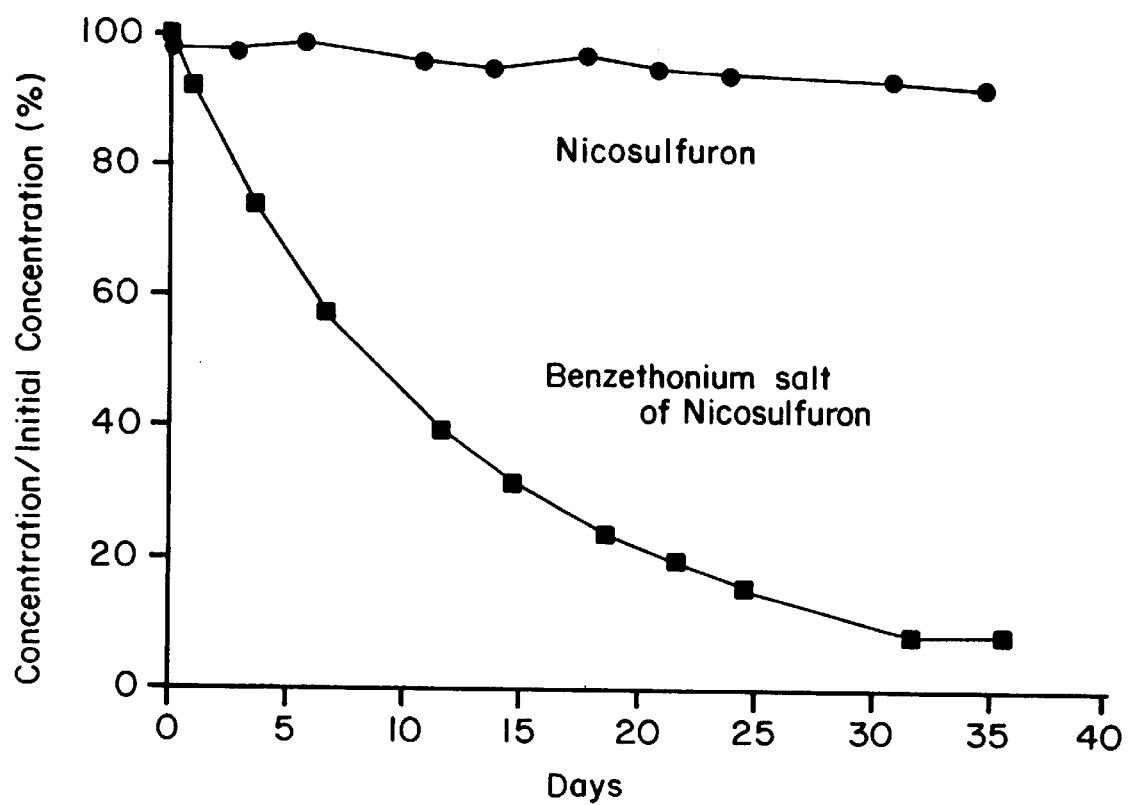
FIG. 2 is a graph of the ratios of the concentrations of benzethonium salt of nicosulfuron and nicosulfuron alone to their initial concentrations versus days in storage as determined by HPLC analysis.

The hydrolytic stabilities of the benzethonium salt of nicosulfuron and its benzethonium salt were determined as follows. Aqueous solutions containing 100 ppm of nicosulfuron or its benzethonium salt were prepared with deionized water and stored at room temperature for 36 days. The solutions were analyzed by HPLC with an Inersil ODS2 column and an ultraviolet detector at a wavelength of 254 nm. The mobile phase through the column consisted of acetonitrile and water at a 1:1 volume ratio. The flow rate through the column was 1 ml/min. FIG. 2 shows the results of the HPLC analysis. The ratio of the concentration of each material after several days storage to the initial concentration of the material is directly proportional to the percentage of material which did not degrade during storage. After 36 days, only 7% of the nicosulfuron was present in the nicosulfuron solution while 92% of the benzethonium salt was present in the benzethonium salt solution.

EXAMPLE 2

Benzethonium salts of rimsulfuron and metsulfuron-methyl were prepared according to the general procedure described in Example 1.

Elemental analysis on the benzethonium salts were performed. The benzethonium salt of rimsulfaron prepared contained 57.10% carbon, 6.90% hydrogen, 9.51% nitrogen, and 7.33% sulfur. Based on the molecular formula, the benzethonium salt of rimsulfuron contains 58.41% carbon, 6.93% hydrogen, 9.97% nitrogen, and 7.61% sulfur. The benzethonium salt of metsulfuron-methyl prepared contained 61.43% carbon, 6.99% hydrogen, 10.20% nitrogen, and 4.01% sulfur. Based on the molecular formula, the benzethonium salt of metsulfuron-methyl contains 62.10% carbon, 7.12% hydrogen, 10.60% nitrogen, and 4.04% sulfur.

EXAMPLE 3

The minimum effective concentrations of the quaternary ammonium salts of the sulfonylureas of Examples 1 and 2 were determined against the fungi *Aspergillus niger* by the zone of inhibition assay method common in the art. *A. niger* ATCC #16404 was contacted with each sulfonylurea salt for 6 days in a Czapek solution agar. The results are shown in Table 1.

TABLE 1

| Sulfonylurea in Benzethonium salt | Minimum Effective Concentration (ppm) |
| --- | --- |
| nicosulfuron | 100–300 |
| rimsulfuron | 100–300 |
| metsulfuron-methyl | 300–1000 |

EXAMPLE 4

The herbicidal efficacy of the benzethonium salts of nicosulfuron and rimsulfuron prepared in Examples 1 and 2 were determined as follows.

Aqueous solutions of the benzethonium salts of each sulfonylurea were prepared with and without 0.25% by weight of the nonionic surfactant polyoxyethylene (20) monolaurate (Tween 20®, trademark of ICI), based upon 100% total weight of aqueous solution. The aqueous solutions were sprayed onto giant foxtail (*Setaria faberi*) and large crabgrass (*Digitaria sanguinalis*) with a spray volume of 187 L/ha (liters/hectare). The active amount of each salt applied in grams/hectare (g/ha) is shown in Table 2 with respect to giant foxtail and Table 3 with respect to large crabgrass. The plants were evaluated two weeks after treatment with the aqueous solution by obtaining their green fresh weights and comparing these weights to an untreated control treatment to compute percent control values. Six replications were made of each treatment. All data were analyzed using a Fisher's Least Significant Difference (L.S.D.) Test at the 0.05 level. The results are shown in Tables 2 and 3.

TABLE 2

*Setaria faberi* (Giant Foxtail)

| Herbicide Treatment | Nonionic Surfactant (Percent by Weight) | % Control |
| --- | --- | --- |
| 3 g/ha Benzethonium salt of rimsulfuron | None | 25 |
| 6 g/ha Benzethonium salt of nicosulfuron | None | 39 |
| 3 g/ha Benzethonium salt of rimsulfuron | 0.25% Tween 20 ® | 95 |
| 6 g/ha Benzethonium salt of nicosulfuron | 0.25% Tween 20 ® | 97 |
| L.S.D. (0.05) | | 12 |

TABLE 3

*Digitaria sanguinalis* (Large Crabgrass)

| Herbicide Treatment | Nonionic Surfactant (Percent by Weight) | % Control |
| --- | --- | --- |
| 10 g/ha Benzethonium salt of rimsulfuron | None | 58 |
| 20 g/ha Benzethonium salt of nicosulfuron | None | 34 |
| 10 g/ha Benzethonium salt of rimsulfuron | 0.25% Tween 20 ® | 94 |
| 20 g/ha Benzethonium salt of nicosulfuron | 0.25% Tween 20 ® | 94 |
| L.S.D. (0.05) | | 12 |

COMPARATIVE EXAMPLE A

The herbicidal efficacy of nicosulfuron and rimsulfuron were determined as follows.

Aqueous solutions were prepared with 75% concentrated, water-dispersible granules (75 DF) of nicosulfuron and rimsulfuron available as Accent® herbicide and Titus® herbicide (trademarks of DuPont) with or without 0.25% by weight of Tween 20®. These aqueous solutions were tested against giant foxtail (*Setaria faberi*) and large crabgrass (*Digitaria sanguinalis*) as described in Example 4. The results are shown in Tables 4 and 5.

TABLE 4

*Setaria faberi* (Giant Foxtail)

| Herbicide Treatment | Nonionic Surfactant (Percent by Weight) | % Control |
|---|---|---|
| 3 g/ha rimsulfuron 75 DF | None | 26 |
| 6 g/ha nicosulfuron 75 DF | None | 31 |
| 3 g/ha rimsulfuron 75 DF | 0.25% Tween 20 ® | 94 |
| 6 g/ha nicosulfuron 75 DF | 0.25% Tween 20 ® | 98 |
| L.S.D. (0.05) | | 12 |

TABLE 5

*Digitaria sanguinalis* (Large Crabgrass)

| Herbicide Treatment | Nonionic Surfactant (Percent by Weight) | % Control |
|---|---|---|
| 10 g/ha rimsulfuron 75 DF | None | 29 |
| 20 g/ha nicosulfuron 75 DF | None | 18 |
| 10 g/ha rimsulfuron 75 DF | 0.25% Tween 20 ® | 89 |
| 20 g/ha nicosulfuron 75 DF | 0.25% Tween 20 ® | 90 |
| L.S.D. (0.05) | | 12 |

The aqueous solutions of the benzethonium salts of each sulfonylurea were as effective as the 75 DF formulations of each sulfonylurea against *Setaria faberi*. The aqueous solutions of the benzethonium salts of each sulfonylurea without the Tween 20® were significantly more effective against Digitaria sanguinalis than the corresponding 75 DF formulations. The aqueous solutions of the benzethonium salts of each sulfonylurea with the Tween 20® were slightly more effective against *Digitaria sanguinalis* than the corresponding 75 DF formulations.

EXAMPLE 5

To 21.57 g 2-[[[[(4,6-dimethoxy-2-pyrimidinyl)amino]carbonyl]amino]sulfonyl]-N,N-dimethyl-3-pyridinecarboxamide and 50 mL 1.0 N NaOH in 1400 mL methylene chloride was incrementally added 22.37 g of diisobutylphenoxy ethoxyethyl dimethylbenzyl ammonium chloride (Hyamine 1622™), with several small methylene chloride washes to facilitate transfer. The reaction medium was filtered through a bed of molecular sieves to remove mineral salts and water. Methylene chloride was stripped to recover the white powder. Upon aging for 1 week at 54° C., 9% relative decomposition of the sulfonylurea resulted as measured by HPLC.

EXAMPLE 6

Into 7.8 g of epoxidized soybean oil (ESBO) was added with stirring: 1.18 g methyl 3-[[[[(4-methoxy-6-methyl-1,3,5-triazin-2-yl)amino]carbonyl]amino]sulfonyl]-2-thiophenecarboxylate tech (98.1%), 1.31 g of anhydrous diisobutylphenoxy ethoxyethyl dimethylbenzyl ammonium chloride in $H_2O$ (Hyamine 1622™), 0.11 g $Ca(OH)_2$, and 0.03 g calcium acetate. The mixture was aged 3 weeks at 45° C. giving 0% relative decomposition of the sulfonylurea as measured by HPLC.

COMPARATIVE EXAMPLE B

Tetradodecyl ammonium bromide was dissolved in 5 mL of $CH_2Cl_2$ and stirred with 3.3 mL of 1 N NaOH. To this was added 1.27 g of N-[[(4,6-dimethoxypyrimidine-2-yl)amino]carbonyl]-1-methyl-4-(2-methyl-2H-tetrazol-5-yl)-1H-pyrazole-5-sulfonamide (97.8%) dissolved in 5 mL of $CH_2Cl_2$ and stirring continued for 5 min at 25° C. The organic phase was separated, washed with water, dried and the solvent removed under vacuum in a rotary evaporator at a maximum of 50° C. The resulting viscous, colorless oil gave an assay of 35% of the corresponding sulfonylurea quaternary salt (vs. 38% theory) using HPLC. This oil was more than 50% soluble in epoxidized soybean oil, methyl caprylate/caprate, and cottonseed oil. 50% solutions of the resultant sulfonylurea quaternary salt in these three solvents were aged 1 week at 54° C., giving 20–45% relative degradation by HPLC analysis. The N-[[(4,6-dimethoxypyrimidine-2-yl)amino]carbonyl]-1-methyl-4-(2-methyl-2H-tetrazol-5-yl)-1H-pyrazole-5-sulfonamide was practically insoluble in these three solvents.

COMPARATIVE EXAMPLE C

In a vial was vortexed the following: 0.214 g methyl 2-[[[[[(4,6-dimethoxy-2-pyrimidinyl)amino]carbonyl]amino]sulfonyl]methyl]benzoate (98.3%),0.192 g of a 25% aqueous solution of tetramethyl ammonium hydroxide, and 4.32 g of water to produce the sulfonylurea quaternary salt. Upon aging the solution at 54° C. for one week, 52% degradation of the sulfonylurea resulted as measured by HPLC.

COMPARATIVE EXAMPLE D

Deionized water (5 g) was saturated with 2-[[[[(4,6-dimethoxy-2-pyrimidinyl)amino]carbonyl]amino]sulfonyl]-N,N-dimethyl-3-pyridinecarboxamide tech (500 ppm) and aged at 25° C. for 30 days. HPLC analysis indicated that 90% relative degradation of the sulfonylurea resulted.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

In the claims:

1. A quaternary ammonium salt of sulfonylurea having the formula

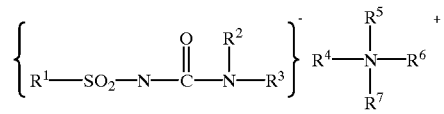

wherein $R^1$ is a substituted or unsubstituted phenyl, heterocyclic ring, or phenoxy, or —$N(CH_3)(SO_2CH_3)$; $R^2$ is H or $CH_3$; $R^3$ is a substituted or unsubstituted pyrimidine or a substituted or unsubstituted triazine; $R^4$ and $R^5$ are independently unsubstituted or hydroxy substituted linear or branched $C_1$–$C_4$ alkyls, —$(CH_2CH_2O)_m CH_2CH_2OH$, or —$(CH_2CHCH_3O)_m CH_2CHCH_3OH$ where m is 1 to 10; $R^6$ is a benzyl, ethylbenzyl, naphthylmethyl, or linear or branched $C_1$–$C_{22}$ alkyl; $R^7$ is —$R^{13}(O)_n(C_6H_5)R^{14}$ where n is 0 or 1; $R^{13}$ is a $C_1$–$C_8$ alkyl or $C_1$–$C_8$ alkoxyalkyl; and $R^{14}$ is a linear or branched $C_1$–$C_{12}$ alkyl.

2. The compound of claim 1, wherein $R^1$ is

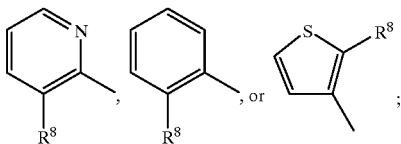

$R^8$ is $CON(CH_3)_2$, $SO_2R^{11}$, or $CO_2R^{12}$; and $R^{11}$ and $R^{12}$ are independently $C_1$–$C_3$ alkyls.

3. The compound of claim 2, wherein $R^1$ is selected from the group consisting of 3-(dimethylamino)carbonyl-2-pyridinyl, 3-(ethylsulfonyl)-2-pyridinyl, 2-carbomethoxyphenyl, and 2-carbomethoxythienyl.

4. The compound of claim 1, wherein $R^3$ is

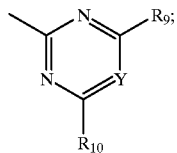

$R^9$ is $CH_3$, $OCH_3$, $OCH_2CH_3$, or $NHCH_3$; Y is CH or N; and $R^{10}$ is $CH_3$ or $OCH_3$.

5. The compound of claim 4, wherein $R^3$ is selected from the group consisting of 4,6-dimethoxy-2-pyrimidinyl and 4-methoxy-6-methyl-1,3,5-triazin-2-yl.

6. The compound of claim 1, wherein said sulfonylurea is selected from the group consisting of 2-[[[[(4,6-dimethoxy-2-pyrimidinyl)amino]carbonyl]amino]suflonyl]-N,N-dimethyl-3-pyridinecarboxamide, N-[[(4,6-dimethoxy-2-pyrimidinyl)amino]carbonyl]-3-(ethylsulfonyl)-2-pyridinesulfonamide, methyl 2-[[[[(4-methoxy-6-methyl)-1, 3,5-triazin-2-yl)amino]carbonyl]amino]sulfonyl]benzoate, methyl ester of 2-[[[[(4-methoxy-6-methyl-1,3,5-triazin-2-yl)methylamino]carbonyl]amino]sulfonyl]benzoic acid, 3-[[[[(4-methoxy-6-methyl-1,3,5-triazin-2-yl)amino] carbonyl]amino]sulfonyl]-2-thiophenecarboxylic, 2-chloro-N-[[(4-methoxy-6-methyl-1,3,5-triazin-2-yl)amino] carbonyl]benzenesulfonamide, methyl 2-[[[[(4-ethoxy-6-(methylamino)-1,3,5-triazin-2-yl)amino]carbonyl]amino] sulfonyl]benzoate, methyl 2-[[[[[4-(dimethylamino)-6-(2,2, 2-trifluoroethoxy)-1,3,5-triazin-2-yl]amino]carbonyl] amino]sulfonyl]-3-methylbenzoate, ethyl 2-[[[[(4-chloro-6-methoxy-2-pyrimidinyl)amino]carbonyl]amino]sulfonyl] benzoate, methyl 2-[[[[(4,6-dimethyl-2 -pyrimidinyl)amino] carbonyl]amino]sulfonyl]benzoate, and N-[[(4,6-dimethoxypyrimidine-2-yl)amino]carbonyl]-1-methyl-4-(2-methyl-2H-tetrazol-5-yl)-1H-pyrazole-5-sulfonamide.

7. The compound of claim 1, wherein said sulfonylurea is selected from the group consisting of nicosulfuron, rimsulfuron, metsulfuron-methyl, tribenuron-methyl, trifensulfuron-methyl, chlorsulfuron, ethametsulfuron methyl, triflusulfuron methyl, chlorimuron ethyl, sulfometuron methyl, bensulfuron methyl, azimsulfuron, flupyrsulfuron methyl, amidosulfuron, iodosulfuron, ethoxysulfuron, prosulfuron, oxasulfuron, primisulfuron, triasulfuron, cinosulfuron, flazasulfuron, halosulfuron, and imazosulfuron.

8. The compound of claim 1, wherein $R^{13}$ is —$CH_2CH_2OCH_2CH_2$—.

9. The compound of claim 1, wherein $R^7$ is [2-[2-(4-diisobutylphenoxy)ethoxy]ethyl].

10. The compound of claim 1, wherein said quaternary ammonium is selected from the group consisting of dialkyl ($C_8$ to $C_{22}$) dimethylammonium, dialkyl ($C_8$ to $C_{22}$) methyl poly(oxyethyl) ammonium, alkyl ($C_8$ to $C_{22}$) benzyldimethyl ammonium, alkyl ($C_8$ to $C_{22}$) trimethylammonium, dialkyl ($C_8$ to $C_{22}$) dihydroxyethyl ammonium, dialkyl ($C_8$ to $C_{22}$) methyl hydroxyethyl ammonium, and alkyl ($C_8$ to $C_{22}$) methyl dihydroxyethyl ammonium.

11. The compound of claim 1, wherein said quaternary ammonium is selected from the group consisting of [2-[2-(4-diisobutylphenoxy)ethoxy]ethyl] dimethylbenzyl ammonium, N,N-didecyldimethylammonium, N,N-dioctyldimethyl ammonium, N,N-octyldecyldimethyl ammonium, octadecyldimethylbenzylammonium, N,N-decylisononyldimethyl ammonium, hexadecyltrimethylammonium, N,N-didecyl-N-methyl-poly (oxyethyl)ammonium, alkyl ($C_{10}$–$C_{18}$) dimethylbenzylammonium, and didecylmethylhydroxyethyl ammonium.

12. A method of preparing a quaternary ammonium salt of sulfonylurea comprising contacting a quaternary ammonium hydroxide with a sulfonylurea to form said quaternary ammonium salt of sulfonylurea, wherein the quaternary ammonium hydroxide has the formula

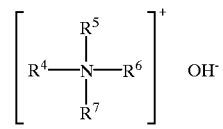

$R^4$ and $R^5$ are independently unsubstituted or hydroxy substituted linear or branched $C_1$–$C_4$ alkyls, —$(CH_2CH_2O)_mCH_2CH_2OH$ or —$(CH_2CHCH_3O)_mCH_2CHCH_3OH$ where m is 1 to 10; $R^6$ is a benzyl, ethylbenzyl, naphthylmethyl, or linear or branched $C_1$–$C_{22}$ alkyl; $R^7$ is —$R^{13}(O)_n(C_6H_4)R^{14}$ where n is 0 or 1; $R^{13}$ is a $C_1$–$C_8$ alkyl or $C_1$–$C_8$ alkoxyalkyl; and $R^{14}$ is a linear or branched $C_1$–$C_{12}$ alkyl.

13. The method of claim 12, wherein said sulfonylurea has the formula

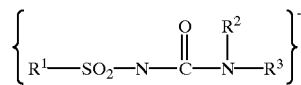

wherein $R^1$ is a substituted or unsubstituted phenyl, heterocyclic ring, or phenoxy, or —$N(CH_3)(SO_2CH_3)$; $R^2$ is H or $CH_3$; $R^3$ is a substituted or unsubstituted pyrimidine or a substituted or unsubstituted triazine.

14. The method of claim 13, wherein $R^1$ is

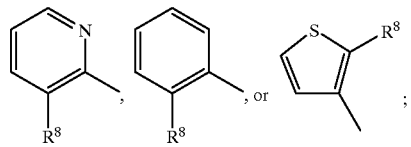

$R^8$ is $CON(CH_3)_2$, $SO_2R^{11}$, or $CO_2R^{12}$; and $R^{11}$ and $R^{12}$ are independently $C_1$–$C_3$ alkyls.

15. The method of claim 13, wherein $R^1$ is selected from the group consisting of 3-(dimethylamino)carbonyl-2-pyridinyl, 3-(ethylsulfonyl)-2-pyridinyl, 2-carbomethoxyphenyl, and 2-carbomethoxythiophenyl.

16. The method of claim 13, wherein $R^3$ is

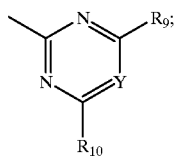

$R^9$ is $CH_3$, $OCH_3$, $OCH_2CH_3$, or $NHCH_3$; Y is CH or N; and $R^{10}$ is $CH_3$ or $OCH_3$.

17. The method of claim 13, wherein $R^3$ is selected from the group consisting of 4,6-dimethoxy-2-pyrimidinyl and 4-methoxy-6-methyl-1,3,5-triazin-2-yl.

18. A pesticidal, herbicidal, fungicidal, or plant growth regulating agent composition comprising an effective amount of one or more compounds of claim 1.

19. A method of controlling plants or fungi or regulating the growth of plants comprising applying an effective amount of one or more compounds of claim 1 to the plants or fungi, the seeds of the plants, or the area on which the plants or fungi grow.

* * * * *